United States Patent [19]

Gentz et al.

[11] Patent Number: 6,147,050
[45] Date of Patent: *Nov. 14, 2000

[54] 5-LIPOXYGENASE-ACTIVATING PROTEIN II

[75] Inventors: Reiner L. Gentz, Gaithersburg, Md.; Robert D. Fleischmann, Washington, D.C.

[73] Assignee: Human Genome Sciences, Inc., Rockville, Md.

[ * ] Notice: This patent is subject to a terminal disclaimer.

[21] Appl. No.: 08/842,234

[22] Filed: Apr. 22, 1997

Related U.S. Application Data

[62] Division of application No. 08/264,003, Jun. 22, 1994.

[51] Int. Cl.[7] .............................. A61K 38/16; C07K 1/00; C07H 21/04; C12P 21/06
[52] U.S. Cl. ......................... 514/2; 530/350; 536/23.5; 435/69.1; 435/325; 435/7.1
[58] Field of Search ...................... 530/350; 536/23.5; 435/69.1, 325, 7.1; 514/2

[56] References Cited

U.S. PATENT DOCUMENTS

| | | | |
|---|---|---|---|
| 5,182,367 | 1/1993 | Gillard et al. | 530/350 |
| 5,229,516 | 7/1993 | Musser et al. | 546/172 |

FOREIGN PATENT DOCUMENTS

98/45436  10/1998  WIPO .

OTHER PUBLICATIONS

Welsch, D. et al., GenBank Database, Accession No. U11552, Oct. 1994.
Nicholson, D. et al., Proc. Natl. Acad. Sci. USA, vol. 90, pp. 2015–2019, Mar. 1993.
Jakobsson, P.–J. et al., J. Biol. Chem., 271:22203–22210 (1996).
Jakobson, P.J. et al., PNAS USA, 89:2521–5 (1992).
Vickers, P.J. et al., Mol. Pharmocol., 42:94–102 (1992).
Vickers, P.J. et al., Mol. Pharmocol., 42:1014–9 (1992).
Bennet, C.F. Et al., Biochem. J., 289 (pt. 1):33–9 (1993).
Rifai, A. Et al., Kidney Int. Suppl., 39:595–9 (1993).
Vickers, P.J. Et al., J. Lipid Mediat., 6:31–42 (1993).

*Primary Examiner*—Ponnathapu Achutamurthy
*Assistant Examiner*—Peter P. Tung
*Attorney, Agent, or Firm*—Human Genome Sciences, Inc.

[57] ABSTRACT

Disclosed is a human FLAP II polypeptide and DNA (RNA) encoding such polypeptide. Also provided is a procedure for producing such polypeptide by recombinant techniques. Further, antagonists against such polypeptide are disclosed. Such antagonists may be used for therapeutic proposes, for example, for treating inflamation, bronchial asthma and may also be used as gastric cytoprotective agents and to treat human glomerulonephritis. Diagnostic assays for identifying mutations in nucleic acid sequences encoding a polypeptide of the present invention and for detecting altered levels of the polypeptide of the present invention are also disclosed.

15 Claims, 3 Drawing Sheets

FIG. 1

```
ATGGCCGGGAACTCGATCCTGCTGGCTGCTGTCTCTATTCTCTCGGCCTGTCAGCAAAGT
 M  A  G  N  S  I  L  L  A  A  V  S  I  L  S  A  C  Q  Q  S

TATTTGCTTTGCAAGTTGGAAAGGCAAGATTAAAATACAAAGTTACGCCCCCAGCAGTC
 Y  F  A  L  Q  V  G  K  A  R  L  K  Y  K  V  T  P  P  A  V

ACTGGGTCACCAGAGTTTGAGAGAGTATTTCGGGCACAACAAAACTGTGTGGAGTTTTAT
 T  G  S  P  E  F  E  R  V  F  R  A  Q  Q  N  C  V  E  F  Y

CCTATATTCATAATTACATTGTGGATGGCTGGGTGTATTCAACCAAGTTTTGCTACT
 P  I  F  I  I  T  L  W  M  A  G  W  Y  F  N  Q  V  F  A  T

TGTCTGGGTCTGGTGTACATATATGCCGTTTCCGACTGAGTCTCGGGATTTGGCCTTGTTGACCCTC
 C  L  G  L  V  Y  I  Y  G  R  H  L  Y  F  W  G  Y  S  E  A

GCTAAAAAACGGATCACCGGTTTCCGACTGAGTCTCGGGATTTTGGCCTTGTTGACCCTC
 A  K  K  R  I  T  G  F  R  L  S  L  G  I  L  A  L  L  T  L

CTAGGTGCCCTGGGAATTGCAAACAGCTTTCTGGATGAATATCTGGACCTCAATATTGCC
 L  G  A  L  G  I  A  N  S  F  L  D  E  Y  L  D  L  N  I  A

AAGAAACTGAGGCGGCAATTCTAA
 K  K  L  R  R  Q  F  *
```

FIG. 2

```
  1 ....MAGNSILLAAVSILLSACQQSYFALQVGKARLKYKVTPPAVTGSPEF   46
         ||   : |||  ||  .|.: |.|  . :  |||   . ||. | :
  1 MDQETVGNVVLLAIVTLISVVQNGFFAHKVEHESRTQNGRSFQRTGTLAF    50

47 ERVFRAQQNCVEFYPIFITILWMAGWYFNQVFATCLGLVYIYGRHLYFWG   96
    ||| :  |||| | |:|||  ||:   ||:| ||| |||.|  ||:|  |
 51 ERVYTANQNCVDAYPTFLAVLWSAGLLCSQVPAAFAGLMYLFVRQKYFVG  100

97 YSEAAKKRITGFRLSLGILALLTLLGALGIANSFLD......EYLDLNIA  140
    |:   .: : |  :|  ||:  :|  | |:|:|:|       |:  :|.
101 YLGERTQSTPGYIFGKRIILFLMSVAGIFNYYLIFFGSDFENYIKTIS    150

141 KKLRRQF...    147
    .: :. :
151 TTISPLLLIP    160
```

Quality:            94.8         Length:            160
Ratio:              0.645        Gaps:                1
Percent Similarity: 51.020       Percent Identity: 34.014

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 444 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 1..441

(xi) SEQUENCE DESCRIPTION: SEQ ID NO:1:

```
ATG GCC GGG AAC TCG ATC CTG CTG GCT GCT GTC TCT ATT CTC TCG GCC        48
Met Ala Gly Asn Ser Ile Leu Leu Ala Ala Val Ser Ile Leu Ser Ala
 1               5                  10                  15

TGT CAG CAA AGT TAT TTT GCT TTG CAA GTT GGA AAG GCA AGA TTA AAA        96
Cys Gln Gln Ser Tyr Phe Ala Leu Gln Val Gly Lys Ala Arg Leu Lys
                20                  25                  30

TAC AAA GTT ACG CCC CCA GCA GTC ACT GGG TCA CCA GAG TTT GAG AGA       144
Tyr Lys Val Thr Pro Pro Ala Val Thr Gly Ser Pro Glu Phe Glu Arg
            35                  40                  45

GTA TTT CGG GCA CAA CAA AAC TGT GTG GAG TTT TAT CCT ATA TTC ATA       192
Val Phe Arg Ala Gln Gln Asn Cys Val Glu Phe Tyr Pro Ile Phe Ile
    50                  55                  60

ATT ACA TTG TGG ATG GCT GGG TGG TAT TTC AAC CAA GTT TTT GCT ACT       240
Ile Thr Leu Trp Met Ala Gly Trp Tyr Phe Asn Gln Val Phe Ala Thr
65                  70                  75                  80

TGT CTG GGT CTG GTG TAC ATA TAT GGC CGT CAC CTA TAC TTC TGG GGA       288
Cys Leu Gly Leu Val Tyr Ile Tyr Gly Arg His Leu Tyr Phe Trp Gly
                85                  90                  95

TAT TCA GAA GCT GCT AAA AAA CGG ATC ACC GGT TTC CGA CTG AGT CTG       336
Tyr Ser Glu Ala Ala Lys Lys Arg Ile Thr Gly Phe Arg Leu Ser Leu
            100                 105                 110

GGG ATT TTG GCC TTG TTG ACC CTC CTA GGT GCC CTG GGA ATT GCA AAC       384
Gly Ile Leu Ala Leu Leu Thr Leu Leu Gly Ala Leu Gly Ile Ala Asn
        115                 120                 125

AGC TTT CTG GAT GAA TAT CTG GAC CTC AAT ATT GCC AAG AAA CTG AGG       432
Ser Phe Leu Asp Glu Tyr Leu Asp Leu Asn Ile Ala Lys Lys Leu Arg
    130                 135                 140

CGG CAA TTC TAA                                                        444
Arg Gln Phe
145
```

(2) INFORMATION FOR SEQ ID NO:2:

(i) SEQUENCE CHARACTERISTICS:
       (A) LENGTH: 147 amino acids
       (B) TYPE: amino acid
       (D) TOPOLOGY: linear (ii) MOLECULE TYPE: protein (xi) SEQUENCE DESCRIPTION: SEQ ID NO:2:

```
Met Ala Gly Asn Ser Ile Leu Leu Ala Ala Val Ser Ile Leu Ser Ala
 1               5                  10                  15
```

```
Cys Gln Gln Ser Tyr Phe Ala Leu Gln Val Gly Lys Ala Arg Leu Lys
            20                  25                  30

Tyr Lys Val Thr Pro Pro Ala Val Thr Gly Ser Pro Glu Phe Glu Arg
        35                  40                  45

Val Phe Arg Ala Gln Gln Asn Cys Val Glu Phe Tyr Pro Ile Phe Ile
    50                  55                  60

Ile Thr Leu Trp Met Ala Gly Trp Tyr Phe Asn Gln Val Phe Ala Thr
65                  70                  75                  80

Cys Leu Gly Leu Val Tyr Ile Tyr Gly Arg His Leu Tyr Phe Trp Gly
                85                  90                  95

Tyr Ser Glu Ala Ala Lys Lys Arg Ile Thr Gly Phe Arg Leu Ser Leu
            100                 105                 110

Gly Ile Leu Ala Leu Leu Thr Leu Gly Ala Leu Gly Ile Ala Asn
            115                 120                 125

Ser Phe Leu Asp Glu Tyr Leu Asp Leu Asn Ile Ala Lys Lys Leu Arg
        130                 135                 140

Arg Gln Phe
145

(2) INFORMATION FOR SEQ ID NO:3:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Asp Gln Glu Thr Val Gly Asn Val Val Leu Leu Ala Ile Val Thr
1               5                   10                  15

Leu Ile Ser Val Val Gln Asn Gly Phe Phe Ala His Lys Val Glu His
            20                  25                  30

Glu Ser Arg Thr Gln Asn Gly Arg Ser Phe Gln Arg Thr Gly Thr Leu
        35                  40                  45

Ala Phe Glu Arg Val Tyr Thr Ala Asn Gln Asn Cys Val Asp Ala Tyr
    50                  55                  60

Pro Thr Phe Leu Ala Val Leu Trp Ser Ala Gly Leu Leu Cys Ser Gln
65                  70                  75                  80

Val Pro Ala Ala Phe Ala Gly Leu Met Tyr Leu Phe Val Arg Gln Lys
                85                  90                  95

Tyr Phe Val Gly Tyr Leu Gly Glu Arg Thr Gln Ser Thr Pro Gly Tyr
            100                 105                 110

Ile Phe Gly Lys Arg Ile Ile Leu Phe Leu Phe Leu Met Ser Val Ala
            115                 120                 125

Gly Ile Phe Asn Tyr Tyr Leu Ile Phe Phe Gly Ser Asp Phe Glu Asn
        130                 135                 140

Tyr Ile Lys Thr Ile Ser Thr Thr Ile Ser Pro Leu Leu Leu Ile Pro
145                 150                 155                 160

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:4:

CGCGGGATCC GCCGGGAACT CGATCCTGCT GCTGGCTGCT     40

(2) INFORMATION FOR SEQ ID NO:5:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCGCAAGCTT AGAATTGCCG CCTCAGTTTC TTGGC     35

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CCGGATCCGC CACCATGGCC GGGAACTCGA TCCT     34

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CACAGGTACC AGCTTCTGCA AGCATTAAAG     30

5-LIPOXYGENASE-ACTIVATING PROTEIN II

This application is a continuation-in-part of U.S. application Ser. No. 08/264,003, now U.S. Pat. No. 5,696,076.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is 5-lipoxygenase-activating protein II "FLAP II". The invention also relates to inhibiting the action of such polypeptides.

Leukotrienes (LTs), formed in granulocytes, monocytes/macrophages and mast cells, mediate immunological and inflammatory responses. Increased levels of LTs in clinical samples implicate these compounds in a number of hypersensitivity and inflammatory diseases, including asthma and inflammatory bowel disease (Ford-Hutchinson, et al., in: Leukotrienes and Lipoxygenases, J. Rokach, ed., Elsevier Science Publishing, New York, 405–425 (1989); Konig, et al., Eicosanoids 3: 1–22; Robinson and Holgate Adv. Prostaglandin Thromboxane Leukotriene Res. 20:209–216, (1990).

Recently, much attention has been given to the LTs as the major pathophysiologic mediators of the inflammatory response since they are much more potent than the prostaglandins (PGs) with regard to increasing vascular permeability, adhesion of leukocytes to the vessel wall, and edema production. Inhibitors of LT synthesis are currently being developed for possible clinical applications as anti-inflammatory agents. Recent studies appear to place the LTs rather than PGs as the most central agents in the etiologic genesis of bronchial asthma. They have been identified as the agents formerly known as slow-reacting substance and have 200 to 20,000 times the bronchoconstrictor activity as histamine. It is currently believed that an LT antagonist or synthesis inhibitor holds great promise in the treatment of bronchial asthma. LTs have been shown to increase insulin secretion and an alternate current hypothesis is that carbohydrate intolerance in some patients with diabetes mellitus may result from an imbalance in the PG to LT ratio in the islet cell.

The first two steps in the biosynthesis of LTs are catalyzed by the $Ca^{2+}$ and ATP-dependent enzyme 5-lipoxygenase (5-LO) which catalyzes the conversion of arachidonic acid to 5-hydroperoxy-6,8,11,14-eicosatetraeonic acid (5HPETE), and subsequently to leukotriene $A_4$ (Samuelson, et al., Science 237:1171–1176, (1987)). Prostaglandins are also synthesized from arachidonic acid precursors. Aspirin-like drugs, and other enzymes, are efficient at preventing prostaglandin synthesis from arachidonic acid to prevent inflammation and generally relieve pain. However, these aspirin-like drugs and other enzymes are ineffective for preventing the synthesis of LTs from arachidonic acid. The $Ca^{2+}$-dependent translocation of 5-LO from the cytosolic to a membrane fraction appears to be a critical step in the activation of the enzyme (Rouzer and Kargman, J. Biol. Chem. 263:10980–10988, Wong, et al., Biochemistry 27:6763–6769, (1988)). Indole and quinoline classes of LT biosynthesis inhibitors and a series of structural hybrids of these compounds block this membrane association but have no significant inhibitory effect on 5-LO in cell free assays. MK-886 (Gillard, et al., Can. J. Physiol. Pharmacol. 67:456–464, (1989)) and MK-0591 (Brideau, et al., Ca. J. Physiol. Pharmacol. 70:799–807, (1992)) are potent members of these inhibitors. FLAP has been identified as the cellular target of this class of inhibitors (Miller, et al., Nature, 343:278–281, (1990)). Inhibitors which bind to FLAP may directly compete with 5-LO for binding to the protein or may cause a conformational change in FLAP leading to a decreased affinity of 5-LO for its membrane binding site.

cDNA clones for FLAP have been isolated from several species (human, mouse, horse, pig, sheep, rabbit, rat and mouse, see: Vickers, et al., Mol. Pharmacology 42:1014–1019 (1992)). The deduced amino acid sequences correspond to hydrophobic proteins with three potential membrane-spanning domains.

In accordance with one aspect of the present invention, there is provided a novel mature polypeptide which is FLAP II, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptide by recombinant techniques.

In accordance with yet a further aspect of the present invention, there is provided a process for utilizing such polypeptide, or polynucleotide encoding such polypeptide to identify substances preventing the interaction of FLAP II with 5-lipoxygenase and to develop inhibitors for the biosynthesis of LTs.

In accordance with yet a further aspect of the present invention, there is provided an antibody against such polypeptides.

In accordance with yet another aspect of the present invention, there are provided antagonists to such polypeptides, which may be used to inhibit the action of such polypeptides, for example, in the treatment of angina, endotoxic shock, inflammatory conditions, such as psoriasis, atopic eczema, rheumatoid arthritis, inflammatory bowel disease, osteoarthritis, tendinitis, bursitis, ulcerative colitis and other immediate hypersensitive reactions, and LT-mediated naso-bronchial obstructive air-passageway conditions, such as allergic bronchoasthma, allergic rhinitis, allergic conjunctivitis, for the treatment of human glomerulonephritis, migraine headaches and as a gastric cytoprotective agent.

In accordance with yet a further aspect of the present invention, there is also provided nucleic acid probes comprising nucleic acid molecules of sufficient length to specifically hybridize to a nucleic acid sequence of the present invention.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

The following drawings are illustrative of embodiments of the invention and are not meant to limit the scope of the invention as encompassed by the claims.

FIG. 1 depicts the polynucleotide sequence and corresponding deduced amino acid sequence of FLAP II. The FLAP II polypeptide as shown is the mature polypeptide consisting of 147 amino acids. The standard one-letter abbreviation for amino acids is used.

FIG. 2 shows an amino acid comparison between FLAP II (upper line) and human FLAP I (lower line).

FIG. 3 illustrates the hydrophobic and hydrophilic portions of human FLAP I and FLAP II.

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75771 on May 12, 1994 with the American Type Culture Collection (ATCC), 10801 University Blvd., Manassas, Va. 20110–2209, USA.

BRIEF DESCRIPTION OF THE DRAWINGS

The polynucleotide of this invention was discovered in a cDNA library derived from aorta endothelial cells induced with tumor necrosis factor a. It is structurally related to the FLAP family. It contains an open reading frame encoding a protein of 147 amino acid residues. The protein exhibits the highest degree of homology to the human FLAP protein with 34% identity and 51% similarity over the entire coding sequence. Further, there is a highly conserved region of FLAP I across many different species (residues 42–61) (Vickers, P. J., et al., J. Lipid Mediat., 6:31–42 (1993)). The sequences of the present invention show significant homology to this conserved region (55%).

The polynucleotide of the present invention may be in the form of RNA or in the form of DNA, which DNA includes cDNA, genomic DNA, and synthetic DNA. The DNA may be double stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

Figure 3:

The above-referenced deposit was deposited with the ATCC, 12301 Parklawn Drive, Rockville, Md. 20852. Since the strain referred to is being maintained under the terms of the Budapest Treaty, it will be made available to a patent office signatory to the Budapest Treaty. If a patent should issue which is directed to the present invention, upon the issuance of such a patent the deposited strain of ATCC 75771 will be irrevocably and without restriction released to the public, excepting for those restrictions permitted by enforcement of the patent.

The polynucleotide which encodes for the mature polypeptide of FIG. 1 (SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or noncoding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a nonnaturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene of the invention including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli$.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli$, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics to human disease.

The present invention is also directed to an assay which measures the ability of compounds to inhibit the interaction of FLAP II with 5-LO. Human osteosarcoma cell lines are transfected with DNA for FLAP II and 5-LO. The cells are then treated with the $Ca^{2+}$ ionophore A23187 resulting in significant production of 5-LO products. Cells are then transfected in the presence of potential antagonist/inhibitor compounds and a comparison is done to determine if the level of 5-LO products is reduced. If so, then the compound is an effective antagonist/inhitor of FLAP II by preventing the interaction of FLAP II with 5-LO.

An example is an antibody against the polypeptide, or in some cases an oligonucleotide, which binds to the polypeptide. Peptide derivatives of FLAP II which have no biological function will recognize and bind to the substrate and thereby prevent the action of FLAP II.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix see Lee et al., Nucl. Acids Res., 6:3073 (1979); Cooney et al, Science, 241:456 (1988); and Dervan et al., Science, 251: 1360 (1991)), thereby preventing transcription and the production of FLAP II. The antisense RNA oligonucleotide hybridizes to the mRNA in vivo and blocks translation of the mRNA molecule into FLAP II polypeptide (Antisense-Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of FLAP II.

Another example of an inhibitor is a small molecule which binds to the active receptor site of FLAP II thereby making it inaccessible to 5-LO such that 5-LO is not activated and does not catalyze the production of LTs. Examples of small molecules include but are not limited to small peptides or peptide-like molecules.

The antagonists may, therefore, be employed to treat angina, endotoxic shock,inflammatory conditions, such as psoriasis, atopic eczema, rheumatoid arthritis, ulcerative colitis and other immediate hypersensitive reactions. These antagonist/inhibitors may also be used to treat LT-mediated naso-bronchial obstructive air-passageway conditions, such as allergic bronchial asthma, allergic rhinitis and allergic conjunctivitis. They may also be employed as gastric cytoprotective agents.

The antagonists of the present invention may also be employed to treat migraine headaches and glomerulonephritis, since LTs cause diffuse inflammatory changes in the glomeruli which leads to proteinuria, hypertension and edema. Diabetes mellitus may also be treated with the antagonists since carbohydrate intolerance in patients with diabetes mellitus may result from an excessive imbalance of LT to PG in the islet cell.

The antagonists may be employed in a composition with a pharmaceutically acceptable carrier, e.g., as hereinabove described.

When the antagonist compounds of the invention are employed in the treatment of allergic airway disorders, as anti-inflammatory agents and/or as cytoprotective agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter, the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also relates to a diagnostic assay for detecting altered levels of FLAP II protein in various tissues since an over-expression of the proteins compared to normal control tissue samples can detect the presence of conditions associated with FLAP II activity. Assays used to detect levels of FLAP II protein in a sample derived from a host are well-known to those of skill in the art and include radioimmunoassays, competitive-binding assays, Western Blot analysis and preferably an ELISA assay. An ELISA assay initially comprises preparing an antibody specific to the FLAP II antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any FLAP II proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to FLAP II. Unattached reporter antibody is then washed out. Peroxidase substrates are then added to the dish and the amount of color developed in a given time period is a measurement of the amount of FLAP II protein present in a given volume of patient sample when compared against a standard curve.

A competition assay may be employed wherein antibodies specific to FLAP II are attached to a solid support and labeled FLAP II and a sample derived from the host are passed over the solid support and the amount of label detected attached to the solid support can be correlated to a quantity of FLAP II in the sample.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Cloning and Expression of FLAP II Using E.coli

The DNA sequence encoding the FLAP II protein, ATCC # 75771, was amplified using PCR oligonucleotide primers corresponding to the 5' and 3' sequences of the gene: The forward primer has the sequence: CGCGGGATCCGCCGG-GAACTCGATCCTGCTGGCTGCT (SEQ ID NO:3).

It contains a recognition site for the restriction endonuclease BamHI followed by 27 nucleotides of the FLAP II gene encoding amino acids 2–10. The AUG codon encoding the first methionine is omitted. An initiation codon is provided by the vector pQE-9 (Qiagen, Inc., 9259 Eton Avenue, Chatsworth, Calif. 91311).

The reverse primer has the sequence: GCGCAAGCTTA-GAATTGCCGCCTCAGTTTCTTGGC (SEQ ID NO:4). It contains the last 24 nucleotides complementary to the 3' end of the FLAP II gene followed by a translational stop codon (underlined) and a recognition site for the restriction endonuclease HindIII (in bold).

The amplified sequences were isolated from a 1% agarose gel using a commercially available kit ("Geneclean" BIO 101 Inc., La Jolla, Calif.). The fragment was then digested with the endonucleases BamHI and Asp 718 and then purified again by isolation on a 1% agarose gel. This fragment is designated F1.

pQE-9 encodes antibiotic resistance (Amp$^r$), a bacterial origin of replication (ori), an IPTG-regulatable promoter operator (P/O), a ribosome binding site (RBS), a 6-His-tag and unique restriction enzyme cleavage sites.

4 $\mu$g of the plasmid pD10 (Qiagen) were digested with the enzymes BamHI and HindIII and then dephosphorylated using calf intestinal phosphatase using protocols known in the art.

The plasmid was then isolated from a 1% agarose gel using the commercially available kit ("Geneclean"). The dephosphorylated vector DNA is designated V1.

The dephosphorylated vector V1 was ligated with the fragment F1 using T4 DNA ligase using procedures known in the art. The ligation mixture was then transformed into *E.coli* M15 (described as strain OZ 291 by Villarejo et al. in J. Bacteriol. 210:466–474 [1974] containing the repressor plasmid pDMI.1 (Certa et al. 1986, EMBO Journal 5:30513056). M15/pDMI.1 contains multiple copies of the plasmid pDMI.1, which expresses the laci repressor and also confers kanamycin resistance (Kan$^r$).

Plasmids of transformed bacteria were then isolated and characterized for the correct insertion of the FLAP II gene using the restriction enzymes BamHI and HindIII. A plasmid was isolated containing the correct insert and called pHIS-FLAPII.

*E.coli* M15 cells containing pDMI.1 were transformed with pHIS-FLAP II and subsequently grown at 37° C. in LB medium (10 g bacto tryptone, 5 g yeast extract, 5 g NaCl per liter) containing 100 mg/l ampicillin and 25 mg/l kanamycin. At an optical density at 600 nm of 0.8 IPTG was added to a final concentration of 2 mM. After additional 2.5 hours at 37° C. the cells were harvested by centrifugation.

The FLAP II protein expressed in *E.coli* was purified by Ni-chelate affinity chromatography. The *E.coli* cells of 1 liter induced culture were lysed by adding buffer A (6 M guanidine-hydrochloride, 0.1 M sodium phosphate, pH 8.0) and stirring the suspension for 2 hours (100 rpm). The suspension was then centrifuged for 10 minutes at 100000× g. The supernatant was loaded onto a column containing 3 ml of the NTA-resin (Qiagen Inc.). Then, the column was washed with 30 ml of buffer A. Subsequently, the column was washed with 20 ml of buffer B (8 M urea, 0.1 M sodium phosphate, 0.01 M Tris, pH 8.0), and then with 20 ml of buffer B, pH 6.5. Finally, the FLAP II protein was eluted with buffer B, pH 4.5. The presence of the FLAP II protein was confirmed by SDS-PAGE, (Laemmli, Nature 227, 680–685 (1970). Descriptions for the purification of various His-tagged proteins can be found in Hochuli et al., J. Chromatography 411:177–184 (1984), Hochuli et al. Bio/Technology 11:1321–1325 and Gentz et al. (1989) Proc. Natl. Acad. Sci. USA 86:821–824.

EXAMPLE 2

Cloning and Expression of FLAP II Using the Baculovirus Expression System

The DNA sequence encoding the full length FLAP II protein, ATCC # 75771, was amplified using PCR oligonucleotide primers corresponding to the 5' and 3' sequences of the gene:

The 5' primer has the sequence CCGGATCCGCCAC-CATGGCCGGGAACTCGATCCT (SEQ ID NO:5), and contains a BamHI restriction enzyme site (in bold) followed by 6 nucleotides resembling an efficient signal for the initiation of translation in eukaryotic cells (J. Mol. Biol. 1987, 196, 947–950, Kozak, M.), and just behind the first 20 nucleotides of the FLAP II gene (the initiation codon for translation "ATG" is underlined).

The 3' primer has the sequence CACAGGTACCAGCT-TCTGCAAGCATTAAAG (SEQ ID NO:6), and contains the cleavage site for the restriction endonuclease Asp718 and 20 nucleotides complementary to the 3' non-translated sequence of the FLAP II gene. The amplified sequences were isolated from a 1% agarose gel using a commercially available kit ("Geneclean," BIO 101 Inc., La Jolla, Calif.). The fragment was then digested with the endonucleases BamHI and Asp 718 and then purified as described in Example 1. This fragment is designated F2.

The vector pRG1 (modification of pVL941 vector, discussed below) is used for the expression of the FLAP II protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and Asp718. The polyadenylation site of the simian virus (SV)40 is used for efficient polyadenylation. For an easy selection of recombinant viruses the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V.A. and Summers, M. D., Virology, 170:31–39).

The plasmid was digested with the restriction enzymes BamHI and Asp718 and then dephosphorylated using calf intestinal phosphatase by procedures known in the art. The DNA was then isolated from a 1% agarose gel as described in Example 1. This vector DNA is designated V2.

Fragment F2 and the dephosphorylated plasmid V2 were ligated with T4 DNA ligase. *E.coli* HB101 cells were then transformed and bacteria identified that contained the plasmid (pBacFLAPII) with the FLAP II gene using the enzymes BamHI and Asp718. The sequence of the cloned fragment was confirmed by DNA sequencing.

5 µg of the plasmid pBacFLAPII were cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBacFLAP II were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-FLAP II at a multiplicity of infection (MOI) of 2. Six hours later the medium was removed and replaced with SF900 II medium minus methionine and cysteine (Life Technologies Inc., Gaithersburg). 42 hours later 5 $\mu$Ci of $^{35}$S-methionine and 5 $\mu$Ci $^{35}$S cysteine (Amersham) were added. The cells were further incubated for 16 hours before they were harvested by centrifugation and the labelled proteins visualized by SDS-PAGE and autoradiography.

EXAMPLE 3
Expression of FLAP II in Mammalian Cells

Fragment F2 described in example 2 was used for the insertion into the mammalian expression vector pCMV11.

Plasmid pCMV11 contains the strong promoter and enhancer of the "major immediate-early" gene of human cytomegalovirus ("HCMV"; Boshart et al., Cell, 41:521–530 (1985)) behind the promoter are single cleavage sites for the restriction endonucleases HindIII, BamHI, Pvull and Asp 718. After the Asp 718 cleavage site there is situated the polyadenylation site of the preproinsulin gene of the rat (Lomedico et al., Cell, 18:545–558 (1979)). The plasmid contains in addition the replication origin of the SV40 virus and a fragment from pBR322 which confers *E.coli* bacteria ampicillin resistance and the replication in *E.coli*. Plasmid pCMV11 was digested with BamHI and Asp718 and then dephosphorylated using calf intestinal phosphatase as described in Example 1. The dephosphorylated vector was thereafter isolated from an agarose gel as described in Example 1.

The vector fragment V3 was ligated with fragment F2, *E.coli* HB101 bacteria were transfonned and the plasmids of the transformed cells isolated by procedures known in the art. By means of restriction analysis and DNA sequencing according to known methods, transformants were identified which contained the plasmid with the insert in the correct orientation. This vector received the designation pCMV-FLAP II.

Transfections of the COS1 (ATCC CRL 1650) Raji-(ATCC CRL 8163) and Jurkart-(ATCC CCL 86) cells with the plasmid pCMV-FLAP II were carried out either according to the lipofection method published by Felgner et al. (Proc. Natl. Acad. Sci. USA 84:7413–7417 (1987)) or by the well known technique using DEAE Dextran (Pharmacia). The expression vector pCMV11 without the FLAP II gene served as a control. 72 hours after the transfections were carried out the cells were harvested and analyzed for the activation of 5-lipoxygenase.

EXAMPLE 4
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer includes a HindIII site. Equal quantities of the Moloney murine sarcoma virus linear backbone and the amplified EcoRI and HindIII fragment are added together in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polypeptide comprising an amino acid sequence selected from the group consisting of:

(a) the amino acid sequence of residues 1 to 147 of SEQ ID NO:2; and (b) the amino acid sequence of residues 2 to 147 of SEQ ID NO:2.

2. The isolated polypeptide of claim 1, wherein said polypeptide comprises the amino acid sequence of residues 2 to 147 of SEQ ID NO:2.

3. The isolated polypeptide of claim 1, wherein said polypeptide comprises the amino acid sequence of residues 1 to 147 of SEQ ID NO:2.

4. The isolated polypeptide of claim 1, wherein said polypeptide is fused to a heterologous polypeptide.

5. An isolated polypeptide comprising an amino acid sequence selected from the group consisting of:

(a) the amino acid sequence of the full-length polypeptide encoded by the human cDNA contained in ATCC Deposit No. 75771;

(b) the amino acid sequence of the full-length polypeptide encoded by the human cDNA contained in ATCC Deposit No. 75771, excluding the N-terminal methionine; and (c) the amino acid sequence of a mature polypeptide encoded by the human cDNA contained in ATCC Deposit No. 75771.

6. The isolated polypeptide of claim 5, wherein said polypeptide comprises the amino acid sequence of the full-length polypeptide encoded by the human cDNA contained in ATCC Deposit No. 75771, excluding the N-terminal methionine.

7. The isolated polypeptide of claim 5, wherein said polypeptide comprises the amino acid sequence of the full-length polypeptide encoded by the human cDNA contained in ATCC Deposit No. 75771.

8. The isolated polypeptide of claim 5, wherein said polypeptide comprises the amino acid sequence of a mature polypeptide encoded by the human cDNA contained in ATCC Deposit No. 75771.

9. The isolated polypeptide of claim 5, wherein said polypeptide is fused to a heterologous polypeptide.

10. A composition comprising the polypeptide of claim 1.

11. A composition comprising the polypeptide of claim 5.

12. A method for producing a polypeptide, comprising:

(a) culturing a host cell under conditions suitable to produce the polypeptide of claim 1; and (b) recovering the polypeptide from the host cell culture.

13. A method for producing a polypeptide, comprising:

(a) culturing a host cell under conditions suitable to produce the polypeptide of claim 5; and (b) recovering the polypeptide from the host cell culture.

14. A method of detecting a polypeptide of claim 1 comprising:

(a) obtaining a biological sample suspected of containing said polypeptide;

(b) contacting said sample with an antibody which specifically binds said polypeptide; and (c) determining the presence or absence of said polypeptide in said biological sample.

15. A method of detecting a polypeptide of claim 5 comprising:

(a) obtaining a biological sample suspected of containing said polypeptide;

(b) contacting said sample with an antibody which specifically binds said polypeptide; and (c) determining the presence or absence of said polypeptide in said biological sample.

\* \* \* \* \*

UNITED STATES PATENT AND TRADEMARK OFFICE
CERTIFICATE OF CORRECTION

PATENT NO. : 6,147,050
DATED : November 14, 2000
INVENTOR(S) : Reiner L. Gentz and Robert D. Fleischmann It is certified that error appears in the above-identified patent and that said Letters Patent is hereby corrected as shown below:

<u>Title page,</u>
Related U.S. Application Data, please remove "[62]   Division" and replace it with -- [62] Continuation-in-part --.

<u>Column 3,</u>
Line 43, please remove "12301 Parklawn Drive, Rockville, MD 20852" and replace it with -- 10801 University Blvd., Manassas, VA 20110-2209 --.

Signed and Sealed this

Seventh Day of May, 2002

Attest:

JAMES E. ROGAN
Attesting Officer  Director of the United States Patent and Trademark Office